(12) United States Patent
Stetter

(10) Patent No.: US 8,426,932 B2
(45) Date of Patent: Apr. 23, 2013

(54) APPARATUS AND METHOD FOR MICROFABRICATED MULTI-DIMENSIONAL SENSORS AND SENSING SYSTEMS

(75) Inventor: Joseph R. Stetter, Hayward, CA (US)

(73) Assignee: KWJ Engineering Inc., Newark, CA (US)

(*) Notice: Subject to any disclaimer, the term of this patent is extended or adjusted under 35 U.S.C. 154(b) by 0 days.

(21) Appl. No.: 13/271,659

(22) Filed: Oct. 12, 2011

(65) Prior Publication Data

US 2012/0050038 A1  Mar. 1, 2012

Related U.S. Application Data

(63) Continuation-in-part of application No. 12/615,110, filed on Nov. 9, 2009, now Pat. No. 8,310,016, which is a continuation-in-part of application No. 11/879, 462, filed on Jul. 17, 2007, now Pat. No. 7,911, 010.

(60) Provisional application No. 61/112,237, filed on Nov. 7, 2008, provisional application No. 61/392,217, filed on Oct. 12, 2010.

(51) Int. Cl.
*H01L 29/82* (2006.01)

(52) U.S. Cl.
USPC .......................................................... 257/415

(58) Field of Classification Search .......... 257/415–420, 257/E29.105, E21.002
See application file for complete search history.

(56) References Cited

U.S. PATENT DOCUMENTS

2008/0294019 A1* 11/2008 Tran .............................. 600/301
2009/0219104 A1    9/2009 Van Beek et al.

* cited by examiner

*Primary Examiner* — Cuong Q Nguyen
(74) *Attorney, Agent, or Firm* — Dinsmore & Shohl LLP

(57) ABSTRACT

A universal microelectromechanical (MEMS) nano-sensor platform having a substrate and conductive layer deposited in a pattern on the surface to make several devices at the same time, a patterned insulation layer, wherein the insulation layer is configured to expose one or more portions of the conductive layer, and one or more functionalization layers deposited on the exposed portions of the conductive layer to make multiple sensing capability on a single MEMS fabricated device. The functionalization layers are adapted to provide one or more transducer sensor classes selected from the group consisting of: radiant, electrochemical, electronic, mechanical, magnetic, and thermal sensors for chemical and physical variables and producing more than one type of sensor for one or more significant parameters that need to be monitored.

16 Claims, 14 Drawing Sheets

APPARATUS AND METHOD FOR MICROFABRICATED MULTI-DIMENSIONAL SENSORS AND SENSING SYSTEMS

CROSS-REFERENCE TO RELATED APPLICATIONS

This application is a continuation-in-part application of copending U.S. Non-Provisional patent Application Ser. No. 12/615,110, filed Nov. 9, 2009, which is a continuation-in-part application of U.S. Non-Provisional patent application Ser. No. 11/879,462, filed Jul. 17, 2007, now granted as U.S. Pat. No. 7,911,010, the entire disclosures of which are hereby incorporated by reference herein. This application also claims priority from U.S. Provisional Patent Application Ser. No. 61/112,237, filed Nov. 7, 2008, and U.S. Provisional Patent Application Ser. No. 61/392,217, filed Oct. 12, 2010, the entire disclosures of which are hereby incorporated by reference herein.

TECHNICAL FIELD OF THE INVENTION

The present invention is directed to microfabricated devices and methods for making them, and more specifically, to a unique apparatus and method for making multiple kinds of sensors on a single platform. Specifically, the present invention is directed to sensors that are tiny and ultra low power as well as low cost, but sensitive to a variety of important chemical and physical parameters and can be used with unique operating protocols and interpretive algorithms to enable smart sensors.

BACKGROUND OF THE INVENTION

Recently there has been renewed interest in sustaining economic growth through utilization of fossil energy resources, such as coal, in an efficient and environmentally responsible manner. Advanced technology for power plants and gasifiers is important for the clean production of electric power, hydrogen generation, gasification of methane, production of industrial chemicals, refined fuels with reduced impact on water resources, solid waste disposal and capture of carbon dioxide generated in the use of fossil fuels. To meet the demand of future energy innovation, these industrial gases will be produced by clean processes. Sensors and controls are important ingredients in any modern process plant and the coal utilization plants will not be different. The development of effective sensors is vital, and such important technology must be available when needed so there is an effective process and rapid public acceptance of fossil energy utilization. Sensors will not only enable the clean, efficient, and low-cost process, but will also provide for safety in the workplace, home and environment. There is a need for sensors to be located as close to the process points as possible for control of the processes. In addition, there is a need for sensors at exit gas streams that feed auxiliary processes for clean-up or conditioning. Moreover, safety sensors in the plant, the surrounding environment and public spaces would help accelerate public acceptability and the pace of coal technology utilization. Safety sensors may also be utilized for medical and health reasons, especially sensors worn by an individual that may provide immediate feedback on the individual's health and safety. The requirements for such sensors typically exceed the capabilities of current sensors. Several major limitations for current process sensors include: potential severe conditions in and near process streams, interferences of the complex process stream components and the desired analytical measurement, slow response times for analytical information, the need for very low operational power requirements making the sensors incompatible with modern wireless systems, and especially the cost of deployment and ownership. Similarly, safety and environmental sensors are typically too costly and lack performance for easy, wide-spread deployment. So not only do sensors need to be cost effective for widespread deployment, but they also have to be simultaneously low power and tiny so they can be easily interfaced to process, safety, health, and environmental systems with and without wireless and other communication interfaces.

One recent innovation in the manufacturing of devices is microelectromechanical systems (MEMS) technology. MEMS technology is based on a number of tools and methodologies, which are used to form small structures with dimensions in the micrometer scale (one-millionth of a meter). Significant parts of the technology have been adopted from integrated circuit (IC) technology. For example, almost all devices are built on wafers of silicon like IC's. The structures are realized in thin films of materials and patterns using photolithographic methods. There are three basic building blocks in MEMS technology: 1) deposit thin films of material on a substrate, 2) apply a pattern mask on top of the films by photolithographic imaging, and 3) etching the film selectively in the mask. A MEMS process is usually a structured sequence of these operations to form actual devices and patterns can be made by either etching or lift off methods.

One of the most basic building blocks of MEMS processing is the ability to deposit thin films of materials that have different properties like insulators, semiconductors, conductors or special reactivity. The thin films can have a thickness anywhere from a few nanometers to several hundred micrometers. Films can subsequently be locally etched or lifted off to form patterns in the MEMS processes some of which are described below.

MEMS deposition technology can be classified into two groups called 1) depositions that happened because of a chemical reaction, such as chemical vapor deposition (CVD), electro deposition, epitaxy, and thermal oxidation; or 2) depositions that occur because of a physical reaction: such as physical vapor deposition (PVD) or casting. The chemical reaction processes exploit the creation or removal of solid materials directly from the surface by chemical reactions and gas and/or liquid interactions with the substrate material. The solid material is usually not the only product formed by the reaction. By-products can include gases, liquids or even other solids. The physical deposition processes have in common that the material deposited is physically moved onto the substrate. In other words, there is no chemical reaction which forms the material on the substrate. In the chemical reaction, a film or deposits can be made by electrodeposition or by thermal reaction of a gas with a hot substrate which are chemical reactions.

Lithography in the MEMS context is typically the transfer of a pattern to a photosensitive material by selective exposure to a radiation source such as light. Photosensitive materials are materials that experience a change in physical properties when exposed to a radiation source. If we selectively expose a photosensitive material to radiation (e.g. by masking some of the radiation), the pattern of the radiation on the materials is transferred to the photosensitive material exposed, as the properties of the exposed and unexposed regions differ. The washing of the unreacted materials leaves behind the patterned material in the desired pattern dictated by the mask. Subsequent depositions allow the layer to contact only the desired portions of the surface and subsequent removal of the photosensitive material allows the patterning of the deposited layer.

In order to form a functional MEMS structure on a substrate, it is necessary to etch the thin films previously deposited and/or the substrate itself. In general, there are two classes of etching processes: 1) wet etching where the material is dissolved when immersed in a chemical solution, or 2) dry etching where the material is sputtered or dissolved using reactive ions or a vapor phase etchant. As one skilled in the art will appreciate, advances in MEMS processing are ongoing and atomic layer deposition, plasma etching, and deep reactive ion etching and such techniques are constantly being advanced and developed to aid in the manufacture of tiny MEMS structures.

It is the desire herein for the development of a unique approach to generate a MEMS sensor platform with widespread applicability with advanced analytical capability and significant commercial potential. As such, there is a need for apparatuses and new methods for microfabricating multi-dimensional nano-sensor platforms. Accordingly, improved apparatus and methods for using the same are desired. Since MEMS processing has the largest applicability and advantage for large applications and not all chemical sensors applications are large, MEMS is not typically applied to the development of many kinds of chemical sensors. Therefore to achieve commercial viability for the MEMS processes with many chemical sensors, it is advantageous to have many sensors capable of being built on the same MEMS platform made with common MEMS processes. In addition to the versatility of the individual MEMS structure, multiple structures on the same die will result in both redundancy for higher reliability and long lifetime as well as each area functionalized differently providing orthogonally responding devices on the same platform. While building tiny MEMS sensors can be achieved, many of the smallest structures can lack stability or corrode or degrade in performance rapidly especially when operated at elevated temperatures and in real environments. Accordingly, there is also a continuing need for a device that it is stable for long lifetimes and yet is still very small and low power in operation.

SUMMARY OF THE INVENTION

The present invention relates to monitoring devices that include a power source, wireless communication equipment, and at least one sensor or sensing system utilizing microelectromechanical systems (MEMS) technology that consumes less than 500 μW of power. The power can be continuous or intermittent and measured as an average power consumed over the sensor lifetime. Data gathered from the at least one sensor or sensing system by using novel operating modes and interpretive algorithms is transferred by the wireless communication equipment to a central communication hub or to a wired or wireless system appropriate to the application.

Another aspect of the invention relates to a method of monitoring personnel by using a monitoring device that includes a power source, wireless communication equipment, and at least one sensor or sensing system utilizing MEMS technology that consumes less than 500 μW of power. Data gathered from the at least one sensor or sensing system is transferred by the wireless communication equipment to a central communication hub or appropriate communications system and/or subsystem. In these applications, easily wearable sensing devices are needed and such capability is enabled by the tiny MEMS sensors, and low power which obviates the need for a small battery or lack of battery, instead utilizing alternatives like power scavenger or power harvester subsystems.

Another aspect of the invention relates to methods and apparatus for microfabricating multi-dimensional multi-use versatile sensor platforms, such as sensor platforms with multiple structures that can sense several simultaneously needed chemical, biochemical or physical variables. One aspect of the invention is a universal microelectromechanical nano-sensor platform. The platform comprises a substrate having a surface with a first insulating surface layer; a microstructure first conductive layer deposited in one or more patterns on the surface to make several elements or devices; a second insulation layer, wherein the insulation layer is configured such that it covers at least some portion of the first conductive layer's one or more patterns; a second conductive layer deposited in one or more patterns to form electrodes, wherein the elements or device can be utilized for sensing; and one or more functionalization layers deposited on at least some portion of the second conductive layer, wherein the functionalization layers are adapted to provide one or more transducer sensor classes selected from the group consisting of: radiant, electrochemical, electronic, chemical, magnetic and thermal class of chemical sensors. The many variants of chemical sensors and applications can give rise to many materials and methods used in construction, examples of which may be found in "*Experimental Methods in Chemical Sensor and Sensor Array Evaluation and Development,*" Chapter 1 in *Materials and Sensor Arrays—Computational and Experimental Selection Methods*, M. A. Ryan, J. R. Stetter, et al., editors, [Book: Joseph R. Stetter, Chapter 1, "*Experimental Methods in Chemical Sensor and Sensor Array Evaluation and Development,*" in "Computational Methods for Sensor Materials Selection, M. A. Ryan, A. V. Shevade, C. J. Taylor, M. L. Homer, M. Blanco, and J. R. Stetter, editors, 2009, pp 3-46. DOI 10.1007/978-0-387-73715-7-1 Copyright Springer Science+Business Media, LLC 2009. ISBN978-0-387-73714-0 (Series INTEGTRATED ANAL. SYSTEMS, R. A. Potyrailo, ed.)] and also [R. J. Aguilar, Zhengchun Peng, P. J. Hesketh; and J. R. Stetter, Ultra-Low Power Microbridge Gas Sensor; *Proceedings of the 218$^{th}$ Meeting of the Electrochemical Society;* Transactions of the Electrochemical Society, 33(8), 245-253 2010; Chemical Sensors 9 and MEMs/NEMS 9, October 2010, Hunter, Hesketh, et al., eds., Pub. By The Electrochemical Society, Pennington, N.J. 08534 ISBN978-156677-827-5. R. Aguilar, Z. Peng, P. J. Hesketh J. R. Stetter, "An Ultra-Low Power Microbridge Gas Sensor," Electrochem. Soc. Trans., 33 (8), 245-253 (2010).], the entire discloures of which are incorporated herein. However, not all combinations of the materials and processes result in an element or device which possesses the surprising combined properties of sensor performance for practical application in modern low power low cost situations and applications. And not all devices can implement the unique operating protocols and smart algorithms that enable automated temperature correction or multigas compositional analysis as does this structure. And not all sensors of the TCD or chemiresistor type have sufficiently low power to work effectively with modern wireless electronics, cellphones, or energy harvesting circuits that are used in many field appliciations.

Another aspect of the invention is a universal microelectromechanical nano-sensor platform. In this embodiment, the nano-sensor platform comprises: a semiconductor substrate including an upper surface, wherein the upper surface comprises an insulator or has an insulator layer thereon; a microstructure conductive layer deposited in a pattern on the surface to make several devices, wherein the conductive layer comprises one ore more filaments, bridges or filament pairs, and wherein the filaments are disposed above and parallel to the substrate configured such that there is an air gap between the filaments and the upper surface of the substrate; wherein the filaments comprise a size/width of less than 10 microns and a thickness of 1 micron or less. In practice, it is often convenient to construct such filament structures such that they exist in the plane of the surface and are undercut to provide a gap between the structure and the surface.

Another aspect of the invention is a universal microelectromechanical nano-sensor platform. The nano-sensor platform comprises: a semiconductor substrate including a surface; a microstructure polysilicon layer deposited in a pattern on the surface to make several devices, wherein the polysilicon layer comprises a first pair of filaments, wherein the filaments are disposed above and parallel to the semiconductor substrate with an air gap between the base of the filaments and the surface of the substrate; an insulation layer, wherein the insulation layer is configured such that the first pair of filaments of the polysilicon layer remain exposed and are not covered by the insulation layer; one or more functionalization layers deposited on the exposed pair of filaments of the polysilicon layer, wherein the one or more functionalization layers are adapted to provide one or more transducer platform classes selected from the group consisting of: radiant, electrochemical, electronic, mechanical and thermal; and wherein at least one pair of the filaments have a width of less than 10 microns. The small size allows a very rapid response measured in nano-seconds that has heretofore not been observed in such chemical sensors as well as simultaneously being of a low power of operation measured in nano-Watts that was heretofore not possible. The specific design used here and the specific characteristics of the layer of materials and their method of fabrication have further allowed a high level of reliability (e.g., layers are put together with the proper stresses and tensions and materials and procedures so as to allow the fabrication of a rugged structure even though the structures are very small). This reliability has been measured exceeding tens of billions of measurement cycles without any significant drift in electronic properties. This has been an issue with other devices in that as they are made smaller, many new types of failure modes cause short lifetimes because of the delamination of layers or corrosion or otherwise degraded structures that lack the stability or the long term lifetime that is important to analytical devices. Therefore, it is desirable that the active element (polysilicon suspended element) be encapsulated by the defect free insulation layers to mitigate degradation with use over time at both low and elevated temperatures and in differing chemical and physical environments.

The apparatus and methods for manufacturing nano-sensor platforms are advantageous for environmental, health, process, and safety monitoring of fluids, especially small molecule gases. It can now be seen that the many different functionalization layers of the same MEMS platform provides for an almost boundless number of sensors and sensor arrays that contain homogenous and/or heterogeneous layers on the exact same MEMS prepared platform with a wide variety of sensing reactions and reactivity. Not only can many sensors be arrayed on a single surface but the present invention allows diverse and different classes of sensors and related devices like pre-concentrators to be prepared on the same substrate with no change to the underlying platform but only a change in the selection of the functionalization layer(s) in the final processing steps. The surprising number of orthogonally reactive sensors and sensor classes on the same platform constitute a new and more powerful sensing capability. In addition to the surprisingly more effective sensing, the new platform allows designs that are ultra low power for portability, versatility, and interface with modern wireless systems for the underlying platform [e.g., leading to potentially higher production volumes] making MEMS fabrication of chemical sensors practical for real-world applications that are low volume, while heretofore only high volume applications were economically possible and commercially viable using MEMS. There are many additional couplings of this technology to the world of sensing such as thermal isolation techniques to achieve lower power, the use of the ever increasing number of possible materials including plastics and composites, flexible circuit materials for construction, and alternative selective and non-selective functionalization layers for use in liquids and gases. Some surprising advantages include the ability to realize simultaneously, the low power, tiny size, high volume, MEMS fabricated devices in a very reliable design and structure that has versatility heretofore not realized. Further, when applied to practical problems, the speed of response, unique operating modes that are steady state and/or time-power dependent, as well as novel interpretive algorithms, enable the sensors to provide outputs that are physically and chemically compensated for more accurate and reliable sensing in real-world applications. These and additional advantages will be apparent in view of the detailed description.

Exemplary smart operational protocol and smart algorithm are discussed in the following paragraph. If we operate the sensing element as a TCD and in a time-dependent signal mode, i.e. where the signal [or property of the sensor such as resistance] is measured over time as the power to the sensor or other influential variable on the signal is changed, then the resulting time dependent data file has information about the gas(es) being sensed and the environmental conditions. One possible variation is to measure the decay curve when the element is turned off or to measure the signal [e.g., resistance] at the hot temperature and at the cold temperature multiple times at multiple temperatures. We have found from calibration curves that there is only one non-variant over time resistance of the element in a given gas [e.g. zero air] at a single temperature and power level. We can designate this, $C_{Tmeas,0}$ and this is found by calibration of the sensing element at various temperatures in zero air. During a measurement, using our novel smart measurement protocol, we obtain $C_{Tmeas,unk}$ and the analytical signal, i.e., the difference in C, or dC, with and without the target gas(es) present in the air is Analytical Signal=$[C_{Tmeas,unk}-C_{Tmeas,0}]$ at the temperature of the measurement and the value for $C_{Tmeas,0}$ is found form the calibration data. In the simplest model of the smart algorithm, the signal is generated at more than one operating temperatures [e.g., different power levels, voltages, or currents]. This can be accomplished rapidly, in microseconds because the sensing elements are very small, fast responding and very low power. Now that the signal is known at more than one measuring power or temperature, we can equate the signal to the concentration of the gas(es) in air. To a first approximation, the signal is the sum of the signal for the individual gas(es) present. Therefore, if we have differing H2 content and He content in air [to continue our example], the signal would be a composite of the two gases and can be expressed as $$[C_{Tmeas,unk}-C_{Tmeas,0}]=C'*[\% H2]+C''*[\% He] \quad \text{Eq. 1}$$

All values taken at the measured temperature. The constants C' and C'' are the calibration constants at the measured temperature for the gases H2 and He, respectively and are obtained from calibration curves for the sensor. The signal and the constants C' and C" are uniquely dependent on the operating conditions selected [in this example we suggested operating at different power or temperatures]. Continuing our example, because we can write the Equation 1 at different conditions [different currents for example] and the constants C' and C" will be unique under each set of conditions, we see that we will have two equation in two unknowns if we write this for two conditions and we can solve the equations uniquely for the concentration of more than both target gases, i.e. % H2 and % He, in our example. Now it will be obvious to one skilled in the art that any combination of gases with the unique set of parameter-dependent constants [the C', C" being temperature dependent in our example] and any parameter that can be operationally varied, temperature, power, flow, etc., can create the information required to not only temperature correct the signal but also then, from multiple measurements in this parameter space, to determine multiple constituents. Also, non-linear and complex dependencies can be envisioned for more complex dependencies as can exist with certain concentrations and certain interactive gases. All that is required is that the number of variables and variability be appropriate to the problem. Selectivity can also be accomplished within this approach since, if the temperature dependence of the signals, dC, and the calibration constant, e.g. C' are identical, it means that the gas must only contain the gas that corresponds to the C' and no other species is present. Conversely, if the temperature dependence is different for the signal from the C', then there must be some other gas present, i.e., some C" or a more complex situation. This situation can then be solved for each constituent if the constants are known through calibration. This is an example of the interpretive capability of this sensor when operated in a smart mode and interpreted using smart algorithms to improve sensitivity, selectivity, and analytical analysis capability for the singular element operated under variable operating conditions.

BRIEF DESCRIPTION OF THE DRAWINGS

While the specification concludes with claims particularly pointing out and distinctly claiming the invention, it is believed the same will be better understood from the following description taken in conjunction with the accompanying drawings in which:

Figure 1:
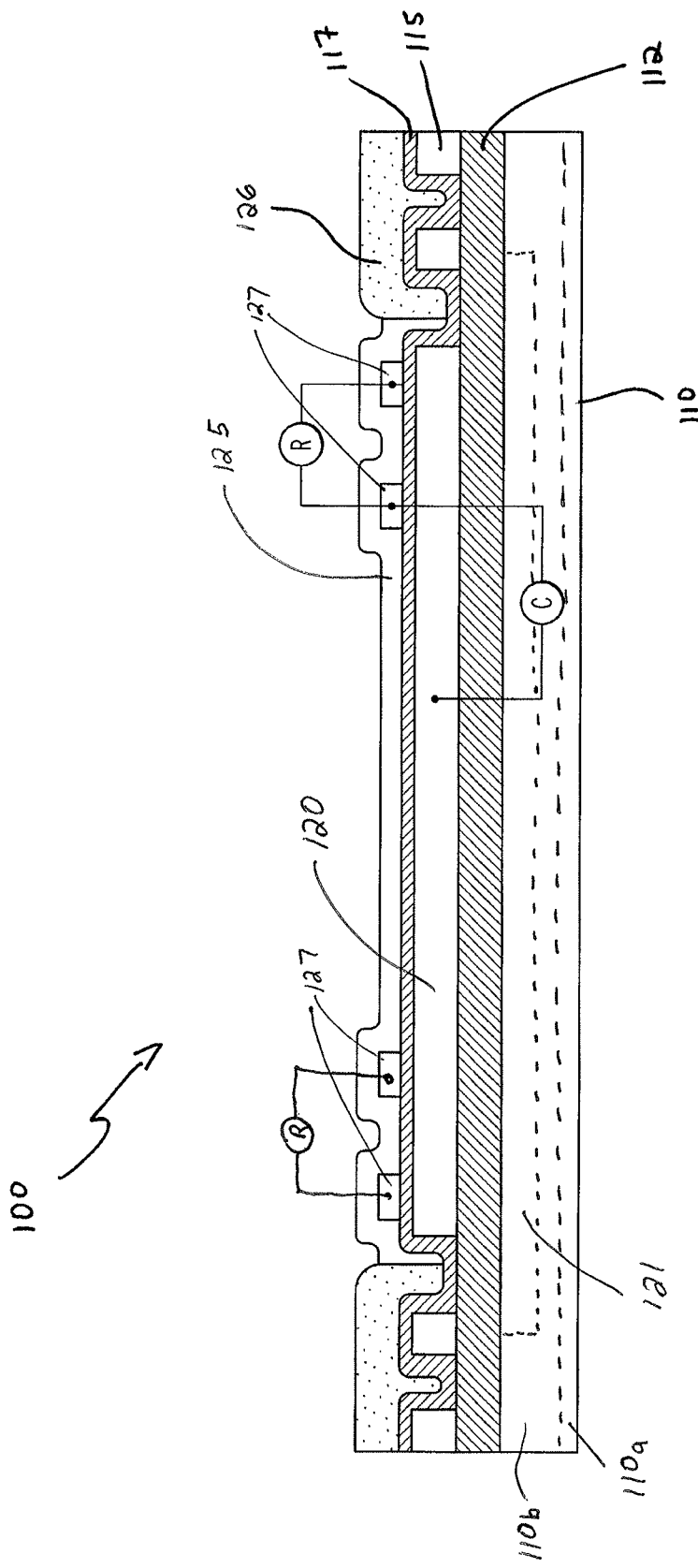
FIG. 1 is a cross-sectional illustration of a microelectromechanical sensor platform according to an exemplary embodiment of the present invention.

The embodiments set forth in the drawings are illustrative in nature, and not intended to be limiting of the invention defined by the claims. Moreover, the individual features of the drawings and the invention will be more fully apparent and understood in view of the detailed description.

DETAILED DESCRIPTION OF THE INVENTION

Reference will now be made in detail to various embodiments which are illustrated in the accompanying drawings, wherein like numerals indicate similar elements throughout the views.

One embodiment of the present invention is the development of microfabricated sensors that can detect critical fluids, especially small molecule gases. Putting this technology into a low-cost MEMS package can add to the unique character of the resulting sensors. These MEMS sensors will be unique because of the combination of high-technological performance, tiny size, low power and low cost and the potential for long lifetime and exceptional stability (which is unique for chemical sensors and significantly increases the ability of these chemical sensors to be part of modern wired and wireless sensing systems).

Described below in varying embodiments are unobtrusive, small, lightweight and energy efficient monitoring devices combining communication equipment and various sensors for detection of important and hazardous gasses, surrounding environmental conditions and personnel vital signs. This unique set of parameters is important for monitoring in many situations including emergency response to fires in civilian and military situations. At least one monitoring device is wirelessly connected to a central communication hub, allowing communication of various data between the at least one monitoring device and the central communication hub. Because embodiments of the monitoring device are small, lightweight and low power, they may be utilized in various fashions or incorporated into various equipments. Non-limiting examples include, but are not limited to, mounting the monitoring device on or within an earpiece, wearing the device on the body of personnel or integration of the device into various personnel clothing or equipment.

Embodiments of the monitoring device may incorporate any unobtrusive, small, light-weight and energy efficient communication equipment, as the particular variety of communication equipment is not vital to the invention. Communication between the monitoring device(s) and the central communication hub may integrate any feasible types of communication, including, but not limited to, radio frequency signal transmission, satellite transmission, any various voice communication channels and combinations thereof. One particular non-limiting embodiment utilizes cellular phone communication. Communication may be carried out in a one-way fashion from either a monitoring device to the central communication hub or vice versa, a two-way fashion allowing back and forth communication between a monitoring device and the central communication hub or in a fashion allowing open communication between multiple monitoring devices and the central communication hub.

Embodiments of the monitoring device may incorporate any unobtrusive, small, lightweight and energy efficient sensor that monitors personnel vital signs. Possible vital sign sensors include, but are not limited to, sensors that monitor heart rate, body temperature, respiration rate, blood pressure, pulse oximetry and any combination thereof. Vital sign sensors may contact the body of the personnel at various points including, but not limited to, the ear, ear canal, neck, chest, stomach, arm, wrist, leg and foot. Vital sign sensors may also be integrated into various personnel clothing or equipment, and thus in some embodiments, not contact the body of the personnel. For example, in certain non-limiting embodiments, a vital sign sensor monitoring personnel breathing rate may be incorporated into an oxygen mask.

Embodiments of the monitoring devices also may incorporate any unobtrusive, small, lightweight and energy efficient sensor that monitors hazardous gasses. Possible important and hazardous gas sensors include, but are not limited to, sensors that monitor oxygen, hydrogen, methane, carbon monoxide, hydrogen sulfide, chlorine, ozone, diesel particulates, gasoline fumes, ethanol and combinations thereof. Embodiments of the monitoring devices also may incorporate any unobtrusive, small, lightweight and energy efficient sensor that monitors surrounding environmental conditions. Possible surrounding environmental condition sensors include, but are not limited to, sensors that monitor temperature, pressure, radiation, moisture and combinations thereof.

One aspect of the invention is a universal microelectromechanical nano-sensor platform. The platform comprises a substrate having a surface with a first insulating surface layer; a microstructure first conductive layer deposited in one or more patterns on the surface to make several devices; a second insulation layer, wherein the insulation layer is configured such that it covers at least some portion of the first conductive layer's one or more patterns; a second conductive layer deposited in one or more patterns to form electrodes, wherein the device can be utilized for sensing; and one or more functionalization layers deposited on at least some portion of the second conductive layer, wherein the functionalization layers are adapted to provide one or more transducer sensor classes selected from the group consisting of: radiant, electrochemical, electronic, chemical, magnetic and thermal chemical sensors.

The sensing films (functionalization layers) can comprise electrolytes and then this sensor can function as an electrochemical sensor for CO, H2S, NOx, EtOH, or any suitable electroactive molecule. In an alternative embodiment, the sensing films (functionalization layers) can be polymers, selective adsorbents, composites, or other sensing materials such that the electronic sensor functions as a chemiresistor, chemicapacitor or an active device like a chemically sensitive transistor as the electronic properties of the functionalization layers are monitored as the target molecule interacts with the sensing film and the electrodes provide means to detect this interaction in an external circuit or recording means.

In one exemplary embodiment, the functionalization layers comprise metal oxide [MOX] materials like SnO2, ZnO2, WO3, and these inorganic coatings will make electronic sensors like chemiresistors to atmospheric gases of all kinds including O2, CO, H2S, NOx, hydrocarbons, H2, or the like. The MOX materials often can be operated at selected temperatures [0-750° C.] in order to adjust reactivity and the above structure allow this controlled operation with heaters and temperature sensors below the functionalization layers.

In another exemplary embodiment, the underlying heater and temperature sensors can be used to control the temperature of operation making the sensor functionalization layers more or less reactive to specific target analytes. In yet another embodiment, the thermal isolation of the active area [heater, temperature sensor, electrodes, functionalization layers] can allow low power operation and fast response and good T control for accurate sensing using temperature dependence of signals. In one exemplary embodiment, the elements are filaments or bridges that are designed to pass current and be heated but are also tiny enough structure to reach high temperatures and have very low power requirements. Also, the filament are capable of being heaters themselves as well as electrodes and can provide surfaces to make sensors that rely on constant or variable temperature control for operation and generation of useful sensing signals.

The Steinhart-Hart equation is a widely used third-order approximation for temperature dependence of resistance of semiconductors:

$$T = \frac{1}{a + b\ln R + c(\ln R)^3}$$

where a, b and c are called the Steinhart-Hart parameters, and must be specified for each device. T is the temperature in Kelvin's and R is the resistance in ohms. To give resistance as a function of temperature, the above can be rearranged into:

$$R = e^{(\beta - \frac{\alpha}{2})^{\frac{1}{3}} - (\beta + \frac{\alpha}{2})^{\frac{1}{3}}}$$

where $$\alpha = \frac{a - \frac{1}{T}}{c} \text{ and } \beta = \sqrt{\left(\frac{b}{3c}\right)^3 + \frac{\alpha^2}{4}}$$

The error in the Steinhart-Hart equation is generally less than 0.02° C. in the measurement of temperature. As an example, typical values for a thermistor with a resistance of 3000 ohms at room temperature (25° C.=298.15 K) are:

$a = 1.40 \times 10^{-3}$ $b = 2.37 \times 10^{-4}$ $c = 9.90 \times 10^{-8}$

More frequently for metals or alloys a first order equation approximated the coefficient of resistance where $(R-R_0)=k*(T-T_{ref})$ that is $dR=K\, dT$ where K is the coefficient of resistance and can be positive or negative. For metals like Pt, K can be 0.003 ohms per degree and a similar value for highly-doped polysilicon, and for metal oxides and low doped-polysilicon the TCR can be much larger and typical of semiconductors and thermistors. It can be an advantage to select materials and designs that are very stable and can operate in the desired temperature range and in the desired matrix [where the fluid is air or liquid]. The resistor can be coated to give it resistance to corrosion and provide other robustness.

In a further embodiment of the present invention, encapsulation between active area and bond pads allows for easy placement of the functionalization layers without shorting of leads to the bond pads. The bond pads allow easy connection to the outside world, i.e. easy packaging into chip carriers, DIP (Dual inline package), TO-type header, and other type packages convenient for use to hook into electronic circuits.

One embodiment of the present invention, a sensor platform 100, is illustrated in FIG. 1. In this embodiment, the sensor platform 100, shown in cross sectional view, comprises a substrate 110 including both a substrate Si wafer 110a with a surface sacrificial layer 110b with a first insulating surface layer 112 on top; a microstructure of first conductive layer 115 deposited in one or more patterns on the surface to make several devices, wherein the first conductive layer 115 comprises a first pair of sensing elements or filaments 120, wherein the filaments are disposed above and parallel to the semiconductor's substrate 110 with an air gap 121 between the base of the filaments and the surface of the substrate created by etching away part of the sacrificial layer 110b in the area under the sensing element which is a part of the conductive layer 115; a second insulation layer 117, wherein the second insulation layer 117 is configured such that the first pair of filaments 120 on the first conductive layer can remain exposed and are not covered by the insulation layer and/or a second set of sensing elements or filaments are covered and encapsulated by top 117 and bottom 112 insulating layers; and on top of the encapsulated (shown) or the unencapsulated filaments there can be none or one or more functionalization layers 125 deposited and touching the exposed pair of filaments 120 of the polysilicon layer that is exposed and not touching when the polysilicon is encapsulated by the second insulating layer. The functionalization layers 125 are adapted to provide one or more transducer platform classes selected from the group consisting of: radiant, electrochemical, electronic, mechanical, and thermal sensors. There is a separate passivation layer 126 that can be used to provide passivation of the leads from the active sensing element are of the chip to the bonding pads and cover any conduction leads on the chip to insure the robustness of the structure.

Figure 2A:
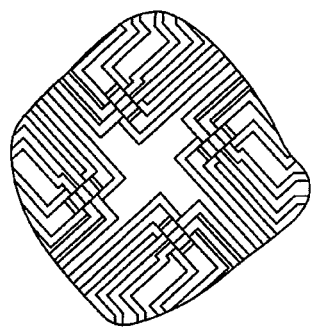
FIGS. 2A-D are top views of patterns of microelectromechanical sensor platforms according to exemplary embodiments of the present invention.
Figure 2B:
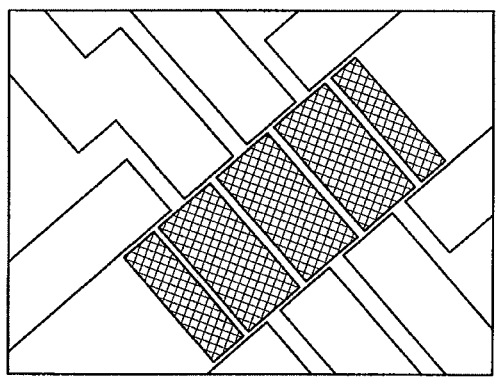
Figure 2C:
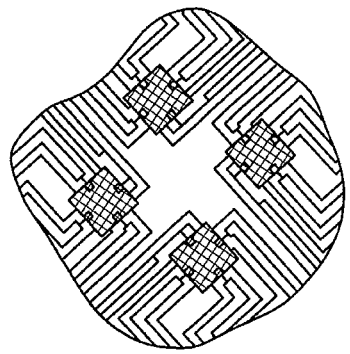
Figure 2D:
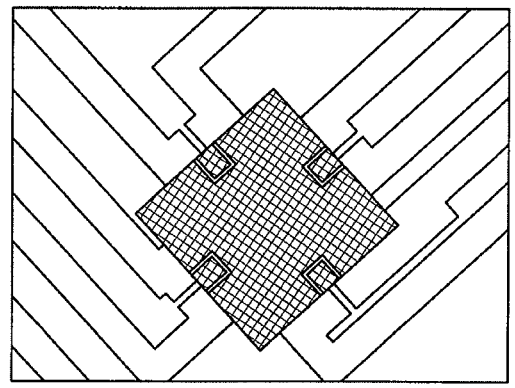

Another embodiment of the present invention is a method of manufacturing the sensor platforms. In this embodiment, the sensor platforms are fabricated by p-type silicon wafers upon which a sacrificial layer of more than two microns of silicon oxide is deposited. In one exemplary embodiment, loop bridges can be fabricated and suspended on the four edges of a square well (FIGS. 2C and 2D) and/or straight bridges (FIG. 2A, 2B, 3), bridging a long, narrow well can be fabricated. The polysilicon conductive portion 120 can be patterned to form loops or bridges of different sizes, such as 1, 5 or 10 microns wide, and 25, 50, or 100 microns long. The polysilicon can be made conductive to different levels by doping and the polysilicon can then be coated with an insulator 117 on top (there is already insulator on the bottom, 112) such as silicon nitride to make them passivated for TCD measurements and in this case the contact 127 and the functionalization layer 125 are not needed for only TCD measurements. The structures can also be coated with aluminum, platinum or Gold or other conductors to make conductive contacts, 127, and then devices can be made thereon with resistive measurements made between and across functional layers as illustrated by the R and C in FIG. 1. The passivation, 112, 117, 126, allows the polysilicon part of the device to be robust. The active element is the part that can be heated and made active for sensing, 120. Selectively etching the conductive and passivation layers creates devices that can be functionalized only in the required active areas for chemiresistor or chemicapacitor or transistor devices independent from the leads and bond pads or in the case of unfunctionalized and encapsulated devices that are thermistor or TCD thermal sensing elements. FIGS. 2A-D illustrates exemplary structures containing 4 bridges with 8 leads or 16 bridges for a total of 32 leads. FIG. 2A illustrates a photomicrograph of the center of a chip area of straight bridges that can be undercut so they are: 1] suspended, encapsulated, and unfunctionalized for TCD applications or 2] suspended, partly exposed and used with functionalizations, or 3] suspended, encapsulated, conductive deposits, 127, for electrodes and functionalized, 125, to create chemiresistors, chemicapacitors, or transistors [active semiconductor devices] on top of the polysilicon which can now function as a bottom gate for transistors or as a heater-temperature controller for sensing devices for example. FIG. 2B is a close-up illustration of straight bridges for one structure of the four areas on the same chip. As one skilled in the art will appreciate, redundant structures allow for easy evaluation, parameterization of response and processing, multiple devices on a single chip, and the estimation of yield and process issues during production. In addition, the cost difference between building one or twenty structures on the substrate in the MEMS world is an insignificant difference. FIGS. 2C and 2D illustrate photomicrographs of loop bridges according to another embodiment of the present invention.

In one exemplary embodiment, active sensing areas are made to contain 4 bridges so that they could be operated in pairs or sequentially for longer lifetime for the device. There are generally multiple areas on each die so that there could be multiple devices on each die.

In an alternative embodiment, the nano-sensor platform can be functionalized with nanostructures such as carbon nanotubes or CNTs and/or composite materials like CNT/polymer mixtures or many different materials to realize humidity and a large number of chemical and biochemical sensors. The functionalization of this MEMS structure with metal oxides can be used to create a versatile number of chemiresistor or chemicapacitor sensors for gases like ozone, CO, or hydrocarbons. In addition, the polysilicon can function as a bottom gate in a bottom gated FET if the polysilicon 120 is encapsulated. Further, because of the multiplicity so easily achieved in MEMS, many of the same kind or many different sensors can be prepared on the same substrate by applying the required functionalizations to different areas of the MEMS die that is populated with one or more of the versatile sensing platforms. It has been shown that heterogeneous electronic noses (containing many differently operating sensors and sensor principles) are more powerful that the homogenous ones, i.e. sensor platforms that can house more than one class of sensors simultaneously are more powerful than those with only a single type of sensor. And, in the description herein, we easily demonstrate electrochemical [amperometric], electronic [chemiresistor], and thermal [thermal conductivity] sensors on a single multifunctional die. In one exemplary embodiment, selective coatings for elevated temperature sensors are possible on the filament/bridge sensors, wherein the coatings are capable of operation at high temperatures with and without the conductor electrode over the insulation layers.

Other exemplary embodiments of the present invention include: The bridges configured with and without insulation and/or protection layers; the bridges configured with and without functionalization layers; on elements without passivation (conductive element exposed) functionalization layers with electrolytes can be used to make electrochemical sensors; functionalization layers with metals such as Pt to make combustible gas sensors; functionalization layers with metal oxides to make electronic sensors like chemiresistors and chemicapacitors and similarly functionalization layers with lower temperature polymers to make chemiresistors and chemicapacitors that function at room temperature; and functionalization layers with sorbents to make preconcentrators.

In one exemplary embodiment, the multiple areas on a single substrate are utilized to make arrays of the same or different devices including sensors, preconcentrators, transistors, or other devices used in fluid analysis and detection.

Figure 3:
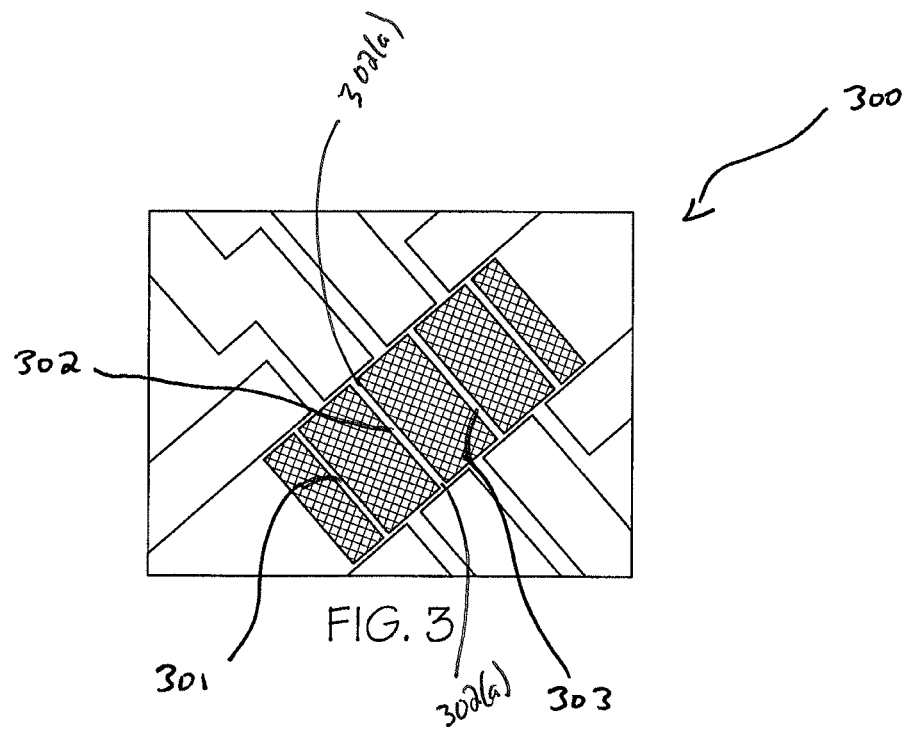
FIG. 3 is a top view of a pattern of a microelectromechanical sensor platform according to an exemplary embodiment of the present invention.
Figure 4A:
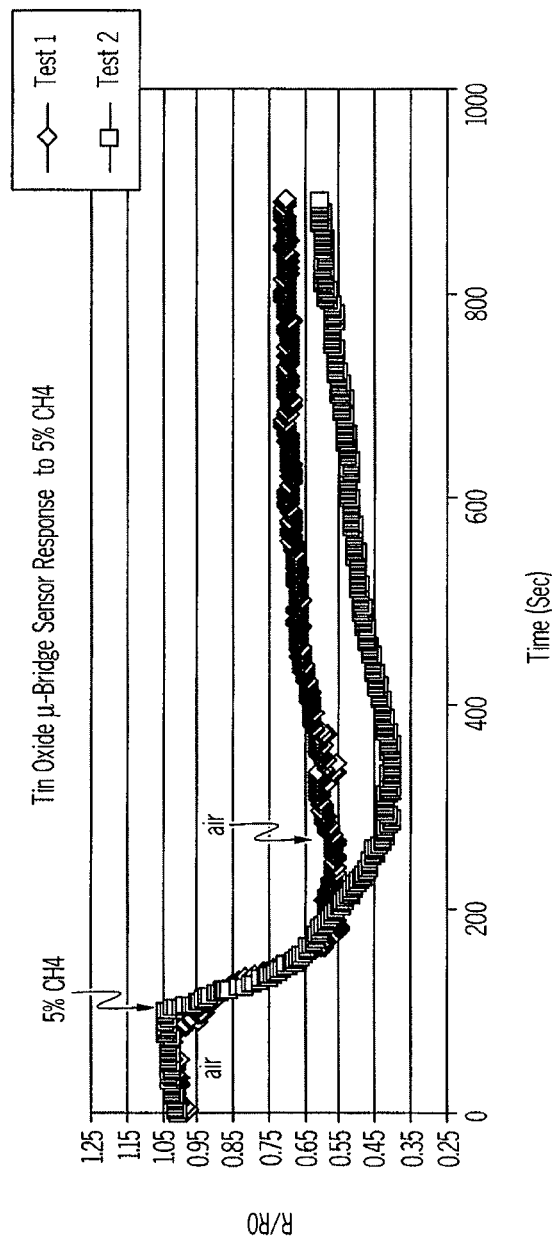
FIGS. 4A-B are sensor response charts relating to exemplary embodiments of the present invention.
Figure 4B:
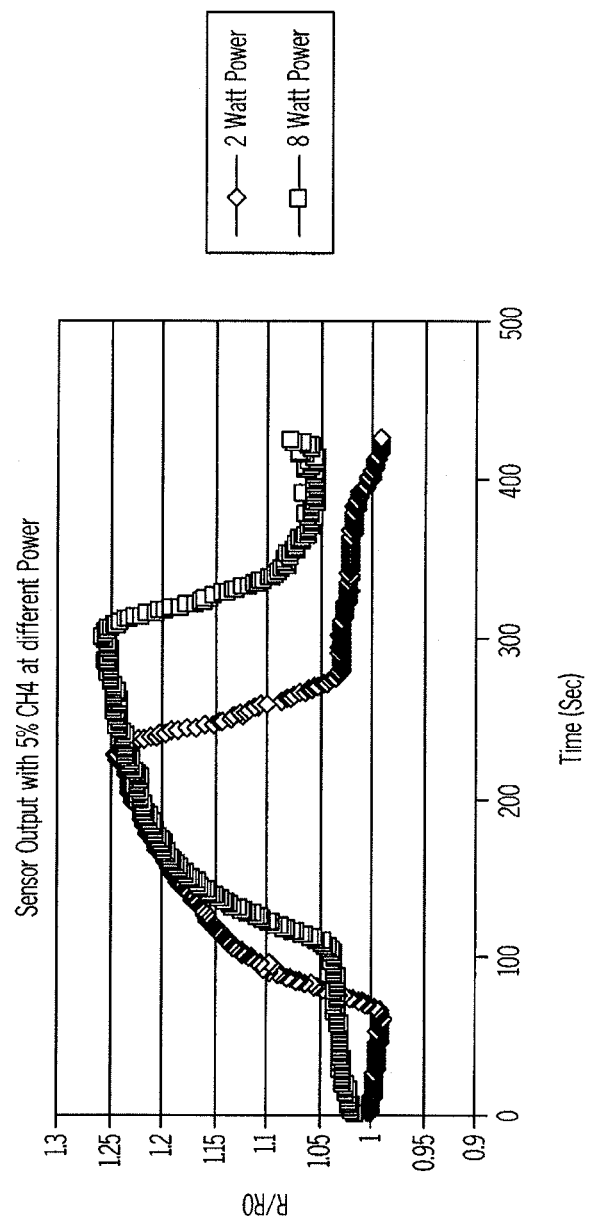

In another embodiment of the present invention illustrated in FIG. 3, a nano-sensor platform 300 is used to fabricate a combustible gas sensor. Bridge number two 302 is functionalized with tin oxide ($SnO_2$) layer. The sensor is then operated by passing current over bridges number one 301 and three 303 to heat the area and measuring the resistance of bridge two 302 (centered between one and three and obviously having means for reading the resistance of the SnO2 layer, e.g., conductive electrodes leads 302a and 302b). In some cases the underlying bridge, 302, can be used as a heater and the SnO2 layer on top, with appropriate conductive leads can be used as the sensing resistor, as this is consistent with the Fig platform possibilities and descriptions. In this exemplary embodiment, the sensor is configured for testing with methane. FIGS. 4A-B illustrates the response of the sensor to 5% methane. As can be noted, the change in resistance is quite large and repeatable on two consecutive tests, but the recovery time may be slow compared to the response time and it is obvious that the devices have not yet been optimized for response to methane in these devices.

Figure 5:
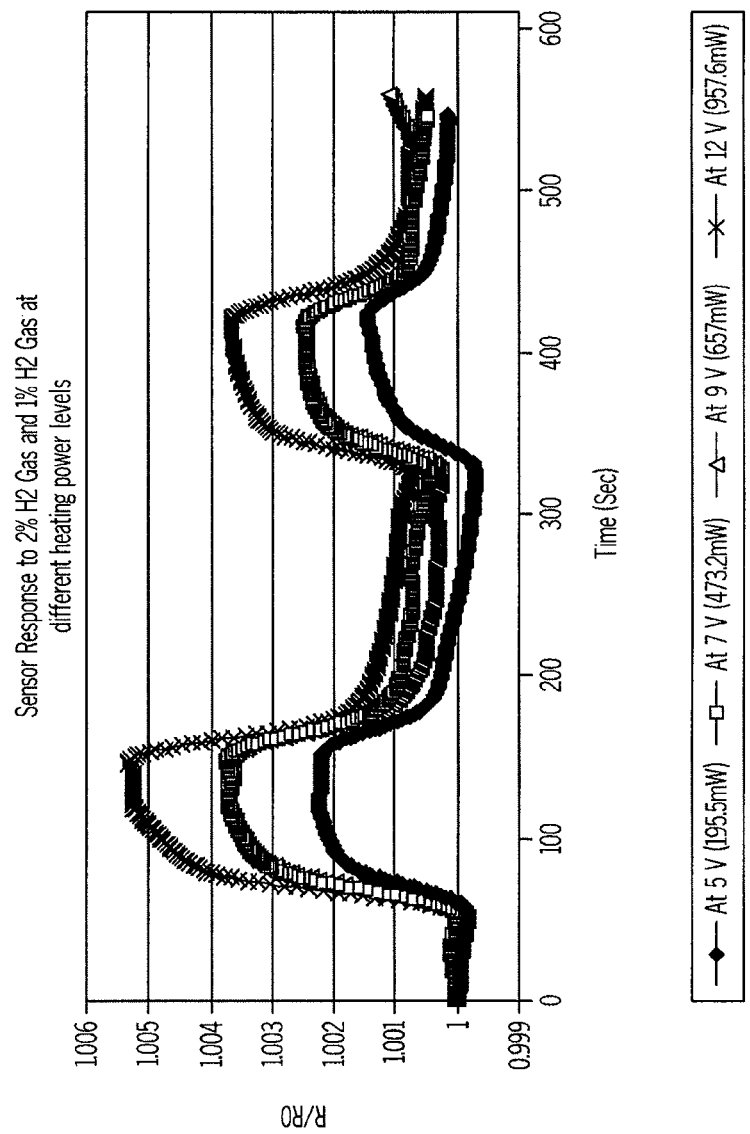
FIG. 5 is a sensor response chart relating to an exemplary embodiment of the present invention.
Figure 11:
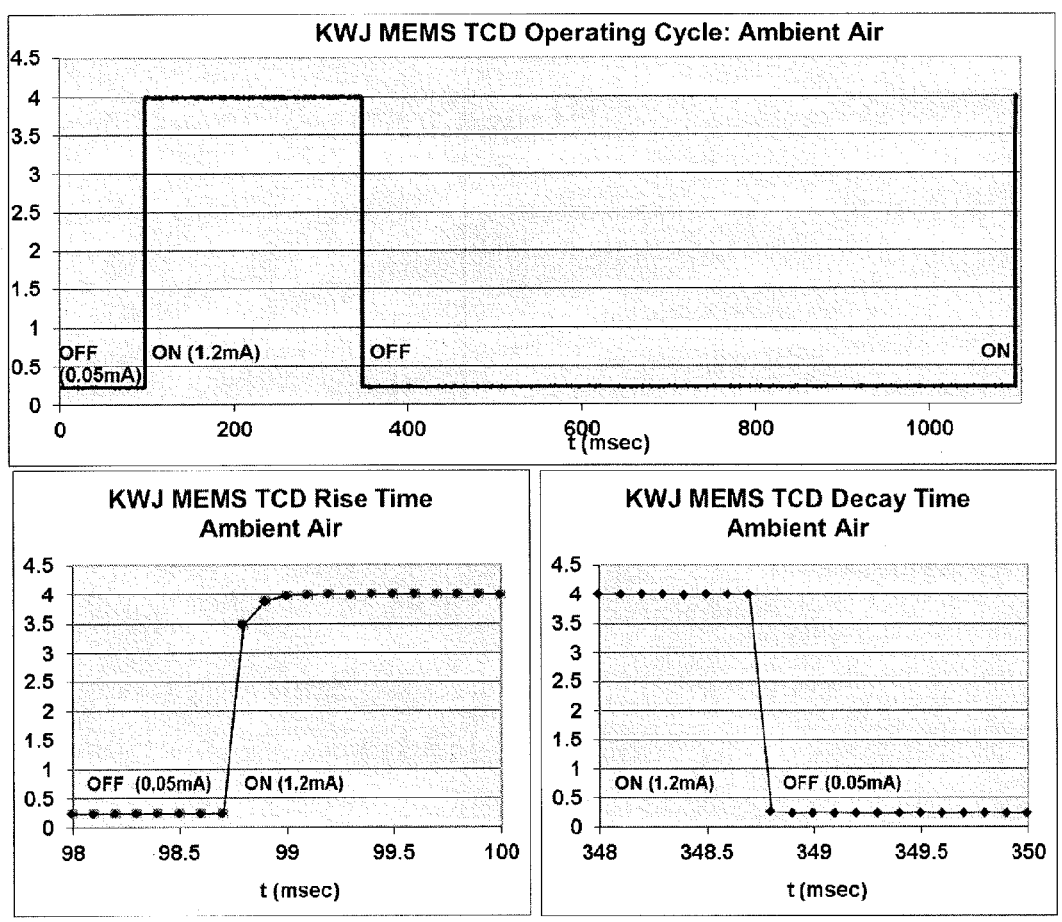
FIG. 11 illustrates sensor response charts relating to exemplary embodiments of the present invention.

In a similar embodiment, a second nano-sensor platform was unfunctionalized and encapsulated so it could act as a TCD element. This bridge was then used as the sensor, and heated to different power levels while exposing the sensor element to different gaseous environments containing hydrogen. FIG. 5 illustrates the response of the sensor to 2% and 1% hydrogen at increasing temperatures (applied power). As can be seen by one skilled in the art, this sensor showed a very rapid response and recovery to hydrogen and the response is most likely limited by the purging of the chamber and not the response time of the tiny MEMS element which we have found to be measured in nanoseconds. The power indicated in the graph legend is total power, across three filaments. One filament consumed approximately 100-200 mW. When the filaments are suspended and thermally isolated, we have found that they consume about 1 mA at 3 V or about 3 mW continuous duty but since they are so fast, they only need to be on for less than a microsecond to take a measurement. In such a case, the device can read once per second using less than 3 nano-watts or 1000 times per second using less than 10 microwatts. In the first experiments reported herein, the structures were not optimized for power consumption or response time, magnitude or selectivity. But rather these experiments demonstrated the feasibility of multi-classes sensors on a single platform. Later experiments have revealed that the sensors with a structure of 1×1×50 microns could detect hydrogen or other gas in air using only about 1 nanowatt of power per reading and with a response time of less than 100 nanoseconds to steady state signal. FIG. 11 illustrates results of these later experiments.

There are many adaptations of these above devices that will allow a variety of sensors and sensing capabilities to be realized. For example the lock and key electrode configuration is particularly suited for chemiresistors and chemicapacitors and electrochemical sensing. The bridges and filament elements are convenient for physical sensors like flow and thermal conductivity or temperature sensing but also can be used as electrodes (when not fully passivated and partially exposed) so that they also are amenable for electronic sensors [chemiresistors and chemicapacitors and active devices like chemically sensitive transistors] and electrochemical sensing. The elements that are filaments are the most versatile and thermal conductivity sensing for gases and binary mixtures is most common and so this new universal MEMS platform will be able to perform many gas analysis problems but with these new structures and implement different methods for analysis with greater versatility, lower power and MEMS advantages [e.g., size, cost] as can be practiced with the invention described herein. The many different fuctionalization layers that are compatible with the MEMS structures herein can create the many devices on a single platform that is truly surprising and novel. For example, functionalization with an electrolyte onto conductive filaments [not covered with insulator] or conductive patterns [lock and key] allow the realization of amperometric electrochemical sensors. Amperometric gas sensors [AGS] can be used for many analytes in gas and or liquid phases at room temperature and elevated temperatures [e.g. fluidic phases of matter]. Coating the same structure with polymers provides electronic sensors that can be used to detect many gases in air and is used frequently in electronic noses. Use as thermal conductivity filaments provides thermal sensors for binary and other gas mixtures. And all three very different sensing mechanisms (amperometry, electronic, thermal sensing) are all on the same platform when constructed as described herein. These sensors have heretofore required different platforms and herein we have a platform that can enable simultaneously electrochemical, thermal and electronic classes of sensors on a single substrate with appropriate functionalization or redundant structures.

Figure 6:
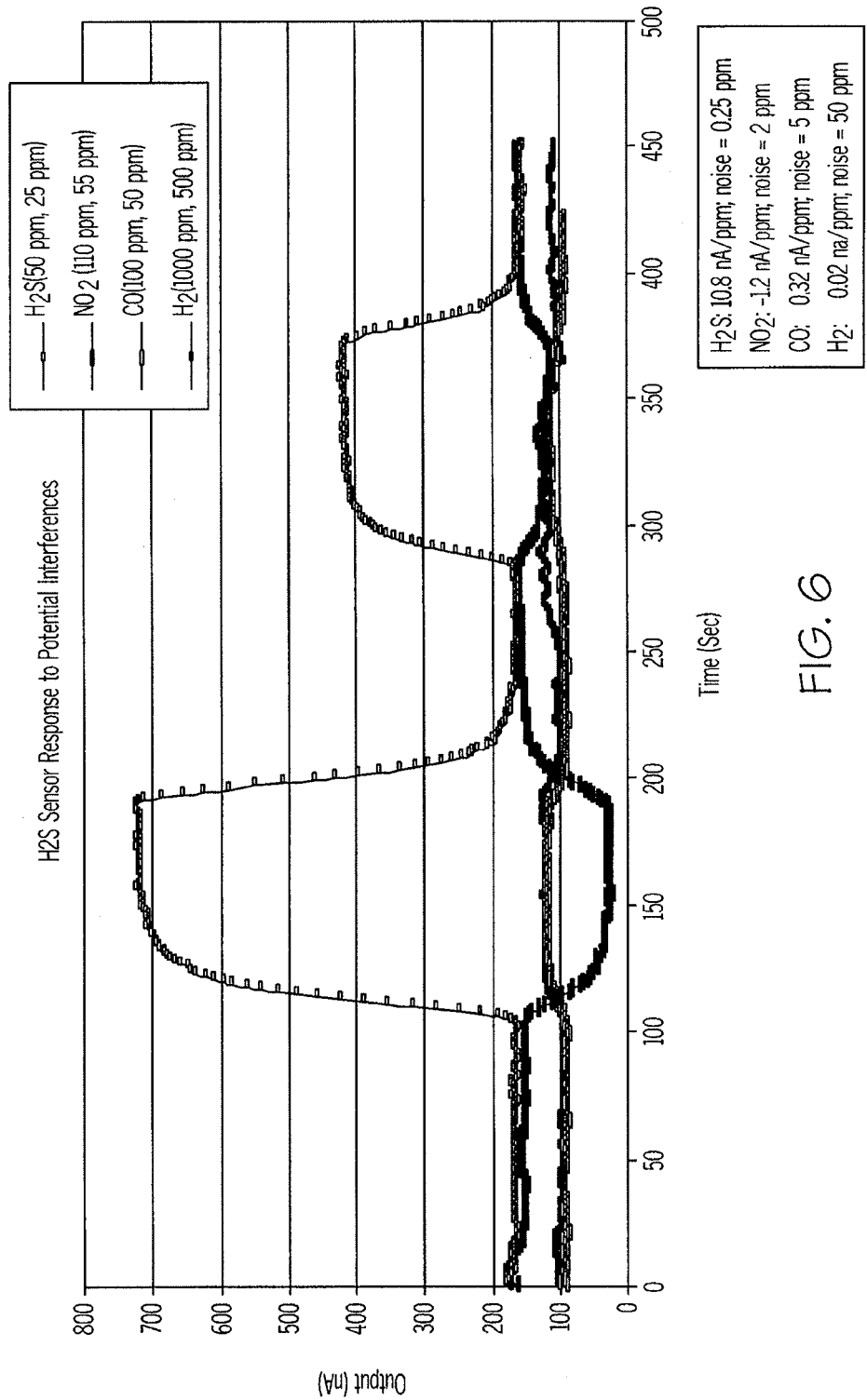
FIG. 6 is a sensor response chart relating to an exemplary embodiment of the present invention.

In one experiment, an electrochemical sensor is created on the platform. In order to create an electrochemical sensor, the bridge is functionalized with a platinum deposition using a proprietary form of the composite. The platinum particles of one micron or less in size (nano-particulate platinum) can be deposited by micro-pipetting onto four different regions of the bridge structure. In this case, the bridge elements serve as electrodes contacting the thin and discontinuous platinum particle film. A thin film of electrolyte (as the functionalization layer) is placed over the surface of the electrodes providing an electrolyte bridge between the platinum particle functionalized polysilicon electrodes. FIG. 6 illustrates the initial results for this functionalized electrochemical system when the sensor is challenged with samples of different electrochemically active gases. The sensor is optimized for $H_2S$ (sensing electrode bias=0 mW vs. Pt/air), and tested with four different gases—hydrogen sulfide, carbon monoxide, nitrogen dioxide, and hydrogen. The electrolyte used for these preliminary tests is a thin film of sulfuric acid, and no effort was made to isolate the referenced electrode. As shown in FIG. 6, the hydrogen sulfide response is quite stable and linear with concentration. Whereas the other three gases show responses of much lower magnitude. The carbon monoxide response on a per ppm basis is several thousand times smaller than the $H_2S$ response, providing excellent selectivity for this sensor. The CO response can be reduced even more with the use of a gold catalyst for the working electrode, and the $NO_2$ response can be minimized with an appropriate sensing electrode bias.

Figure 7:
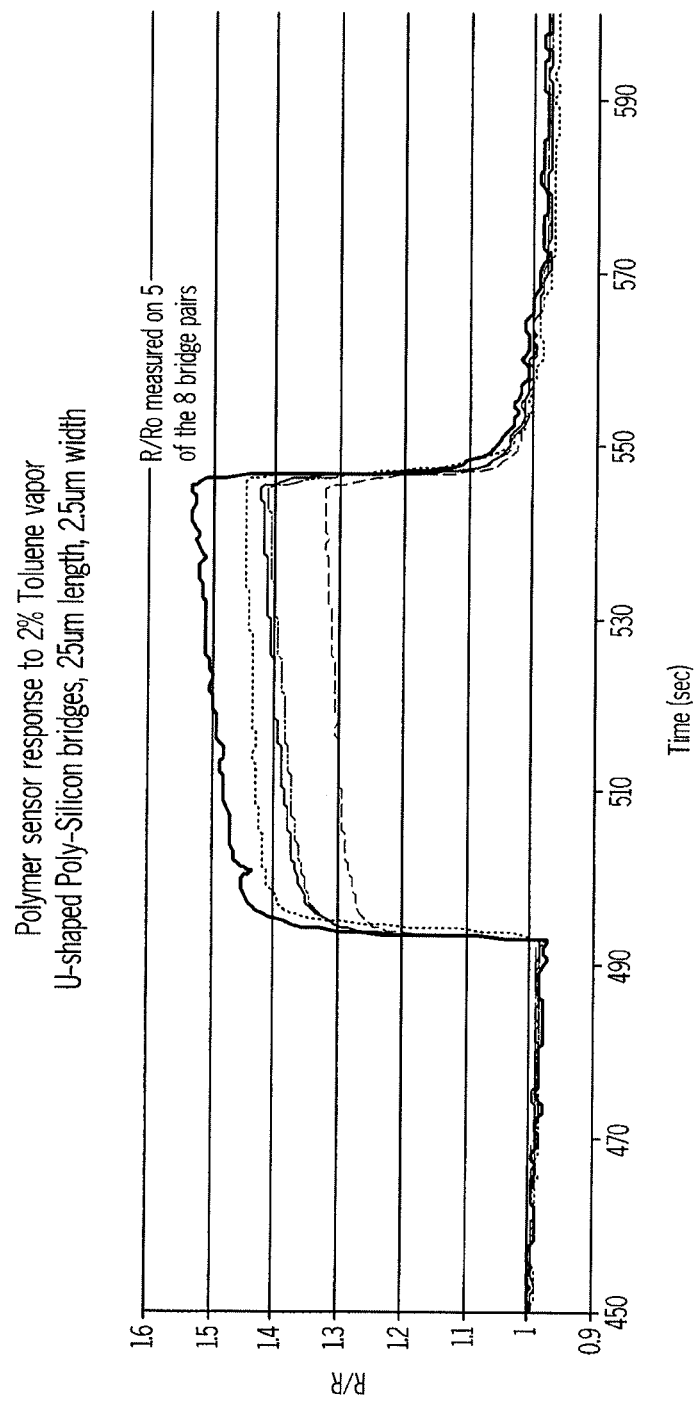
FIG. 7 is a sensor response chart relating to an exemplary embodiment of the present invention.

Yet another experiment on this same platform sensor was conducted to create a conductive polymer sensor on the sensor platforms of the present invention. To test a third sensor class on the same micro-bridge platform, a polymer bridge with nano-particulate carbon and with single walled carbon nano-tubes was coated on the MEMS sensor platform. This sensor will absorb vapor molecules, for example toluene, and exhibited a change in physical properties such as resistance or capacitance. In this experiment, the resistance of the film was monitored when the sensor is exposed to toluene vapors. The change in resistance as measured across five of the eight bridge pairs while the device was exposed to approximately one percent (or 10,000 PPM). The response from these five functionalized layers is shown in FIG. 7. Signals were obtained from three carbon materials: nano-particles, nano-structured carbon, and purchased single wall carbon nanotubes that are 90% pure. All formulations produced responses as illustrated in FIG. 7.

As can be seen from the experiments above, the polysilicon bridges form the foundation for multiple classes of sensors. In the experiments above, three classes of sensors were demonstrated, thermal (catalytic and thermal conductivity), electronic (heated metal oxide or mox, and polymer or polymer composite chemiresistors), and electrochemical (amperometric sensor for $H_2S$ and other electro-active gases).

The present invention comprises a single platform having an electrode array on a dielectric material compatible with several sensor classes with various patterning of electrodes, passivation and encapsulation, and functionalization layers that enable different sensor classes and types to be built on the same platform with the distinction of being thermally isolater and low power and small in size. Thus, the same single platform can have multiple functionalization layers and different classes of sensors addressing different target analytes with different specifications. In one exemplary embodiment, the devices formed on the platform are configured such that they operate in an elevated temperature at very low power, such as less than ten mW and recently less that 1 mW continuous, or a few microwatts in intermittent operation.

Figure 8A:
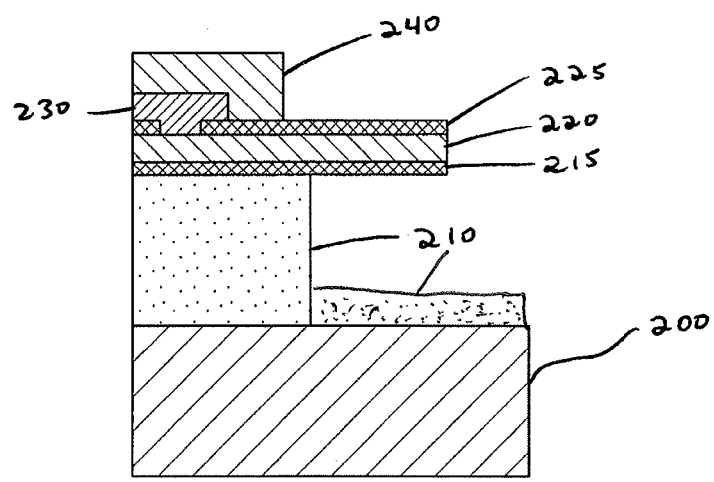
FIGS. 8A-B are cross-sectional illustrations of microelectromechanical sensor platforms according to exemplary embodiments of the present invention.
Figure 8B:
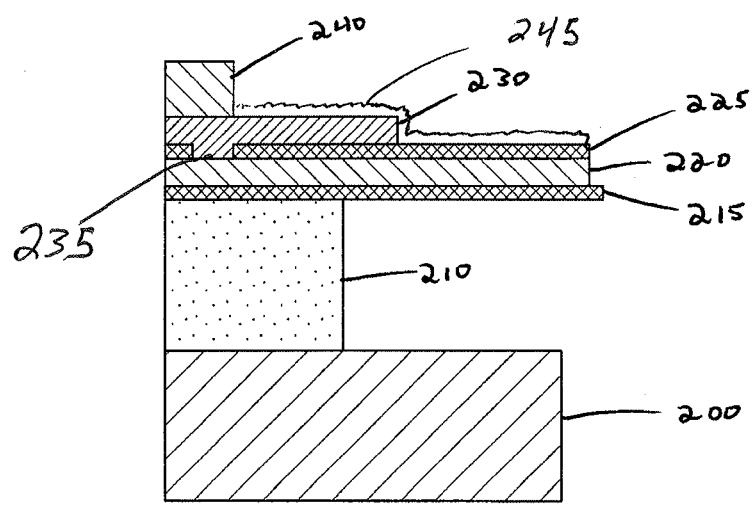

One embodiment of the present invention is illustrated in FIG. 8A. In this embodiment, a micro-bridge sensor chip platform cross section where the sensing element 220 meets the edge of the substrate 200 (to the left) and is extended over the open area to the right is illustrated. FIG. 8A illustrates a cross-section of a bridge platform according to one embodiment of the present invention. The platform of exemplary FIG. 8A is passivated or encapsulated by insulating layers 215 and 225. In this embodiment, the universal microelectromechanical nano-sensor platform comprises a semiconductor substrate including a surface, such as a silicon wafer 200, a micro-structure sacrificial silicon dioxide layer 210 deposited in a pattern on the surface of the substrate silicon wafer 200. In the middle of the silicon nitride layers 215 and 225 is our patterned polysilicon layer of the sensing element layer that is patterned so as to make several devices wherein the polysilicon layer 220 is doped to the desired conductivity level to create the bridges as indicated by the structure comprised of 215 and 220 and 225 suspended over the substrate 200 wherefrom part or all of the sacrifical layer 210 has been selectively removed. The silicon nitride layer 215 is a passivation layer for the silicon oxide 210 and forms an encapsulation layer for the polysilicon layer 220 that can be deposited on top of 215. The polysilicon layer 220 is conductive, and can be used as resistive heaters, temperature measurement, and as electrodes (when part of the element is exposed to the functionalization layer). The platform further comprises another layer of silicon nitride 225 over the polysilicon, etched to have an opening to allow an aluminum layer 230 to be an electrical contact with the polysilicon layer 220 in the region that is not suspended. The Al electrode has contact with the poly through such holes from the sensing element to the bonding pad area of the chip and many metals can be used including Pt, Au, Pd or Al. In one exemplary embodiment, an encapsulation layer 240 is placed over the aluminum layer 230 to provide environmental and other protections to the layer. Of course, other layers are possible depending upon the maximum temperature of operation and the environment for the sensor that is expected. Another exemplary embodiment is illustrated in FIG. 8B, in which the platform electrode runner 230 is not completely passivated and the contact with the substrate through layer 235 is optional. In this case the conductive element 220 can act as a heater and or temperature sensors and the contact metal 230 can act as an electrode in contact with any suitable functionalization layer 245. Further, it may be important that the elements be constructed from layers of materials put down under tension so that stress does not cause early failure of heated devices. In fact, recent measurements have been made to show that this approach, heretofore unknown, is essential to long time trouble free operation of such a tiny device made from these thin layers. We further know that annealing of the layers is also important to final sensor performance.

In one exemplary embodiment, the sensor platform comprises one or more electrodes having polysilicon bridges and the electrodes are functionalized and have a width of one micrometer wherein the sensor platform has power consumption well below 50 mW. In recent measurements the 1×1×50 micron element has a power requirement of 1.2 mA at 3 volts or about 3.6 mW continuous operation but since the element operate with a response time of 100 nanoseconds or less, the device can take one reading per second for a power budget of less than a nanowatt per reading (thus powered at 1 nanowatt with one reading per second or 1 microwatt with 1 reading per millisecond and these rates are often perfectly acceptable for gas detection and monitoring). In another embodiment, the polysilicon sensing element [suspended and thermally isolated bridge structure] is functionalized with a catalyst, wherein the catalysts is configured such that the polysilicon bridge becomes a combustive gas sensor. This CGS can also be operated at very low power, much lower that any such device heretofore [the typical CGS uses about 1 W continuous power and has a slow response time].

Figure 9A:
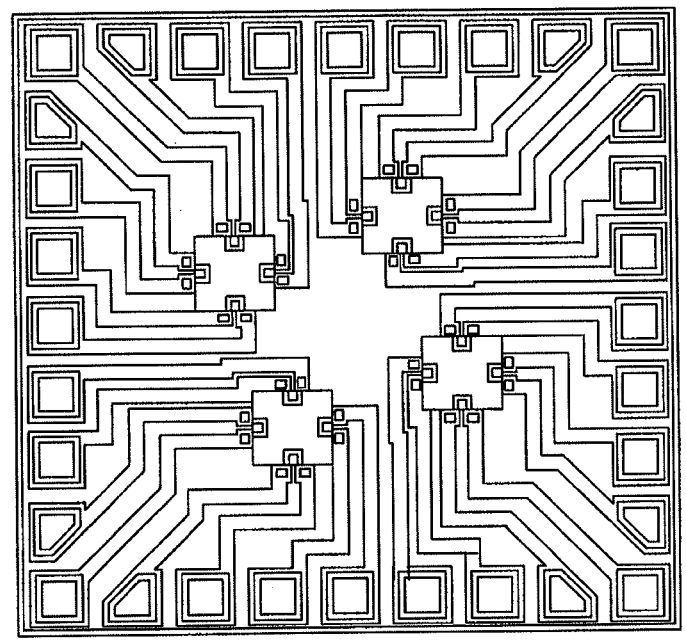
FIGS. 9A-B are top views of patterns of microelectromechanical sensor platforms according to exemplary embodiments of the present invention.
Figure 9B:
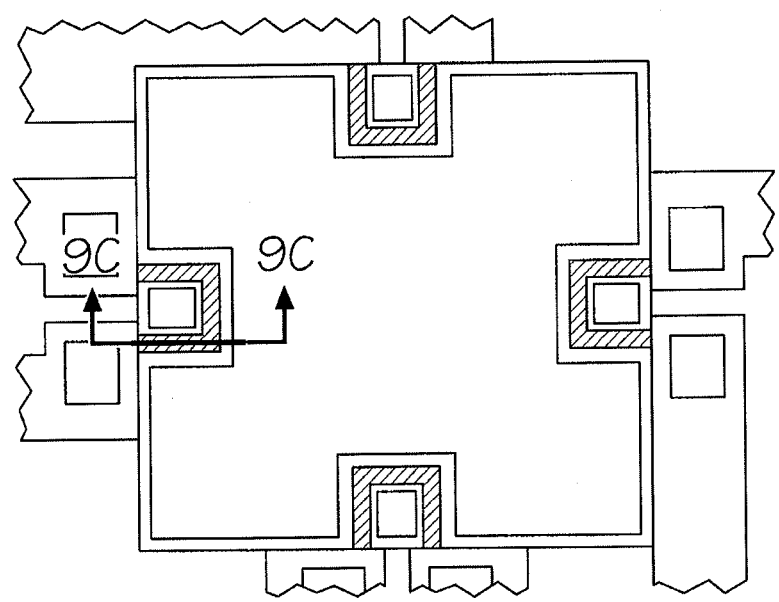
Figure 9C:
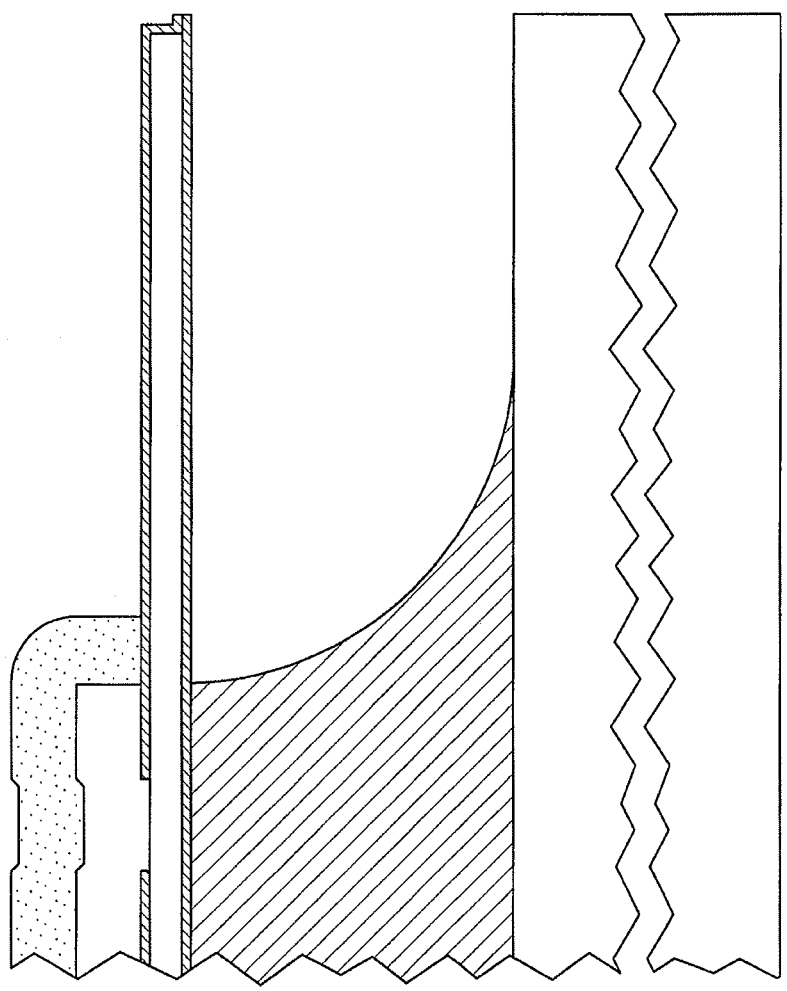
FIG. 9C is a cross-sectional illustration of a microelectromechanical sensor platform according to exemplary embodiment of the present invention.
Figure 9D:
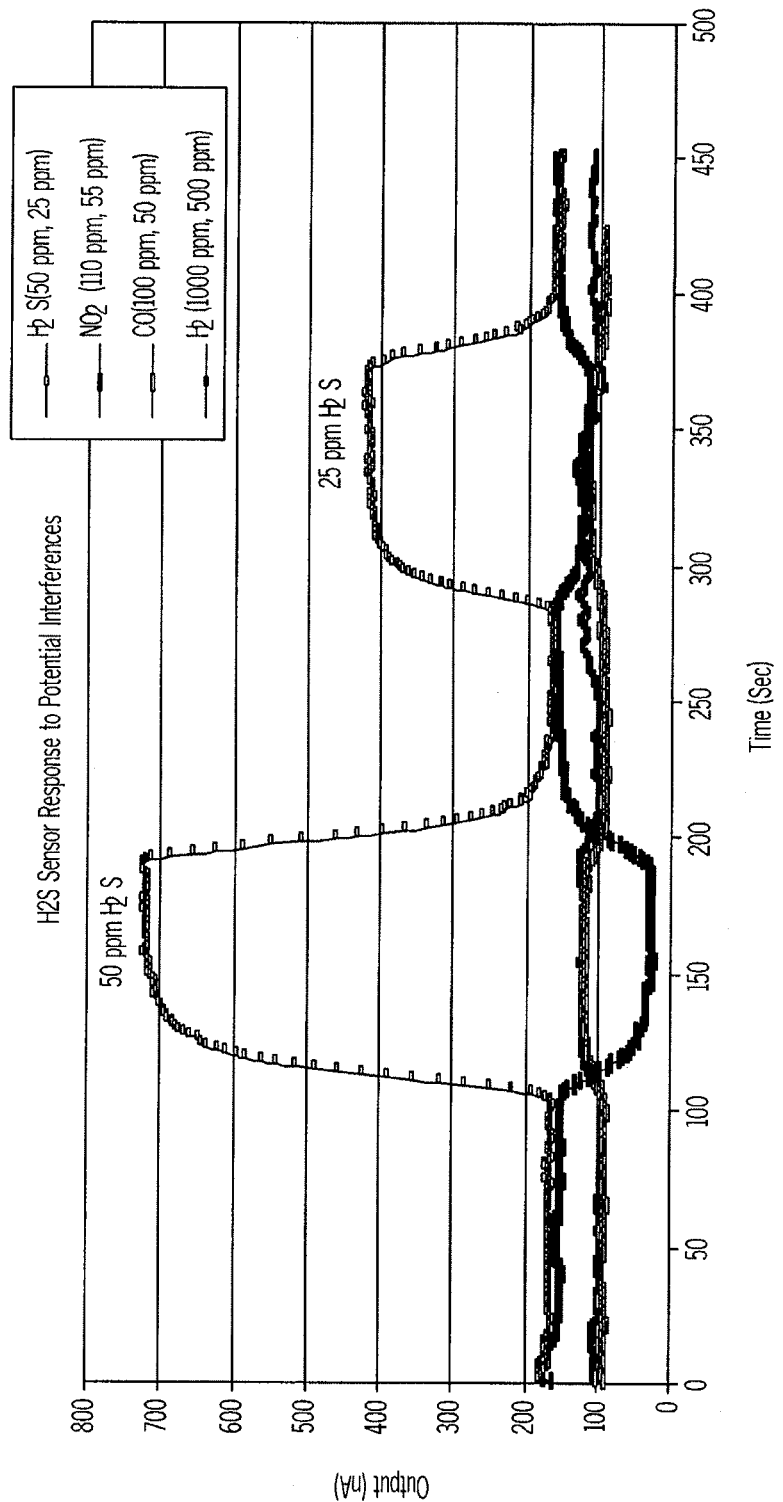
FIG. 9D is a sensor response chart relating to an exemplary embodiment of the present invention.

Illustrated in FIGS. 9A-C is another exemplary universal MEMS nano-sensor platform according to an embodiment of the present invention. In this embodiment, the sensor contains electrodes on a substrate. In one exemplary embodiment, the substrate contains a heater and a temperature sensor. The universal MEMS nano-sensor platform has a thermal sync configured for optimal/minimum power use at a given temperature. The platform comprises one or more sensing layers which are designed for multiple use, such as electrochemistry, electronic and thermal sensing. One or more functionalization layers are added to the sensing layers, and these functionalization layers add sensitivity, selectivity, and encapsulation from environmental insult. The MEMS chemical platform can detect virtually all the chemical analytes required in coal gasification: methane and hydrogen in thermal sensors, $H_2S$, carbon monoxide (CO), $NO_x$, $NH_3$, $Cl_2$, electrochemically, and hydrocarbons with electronic sensors.

Figure 10:
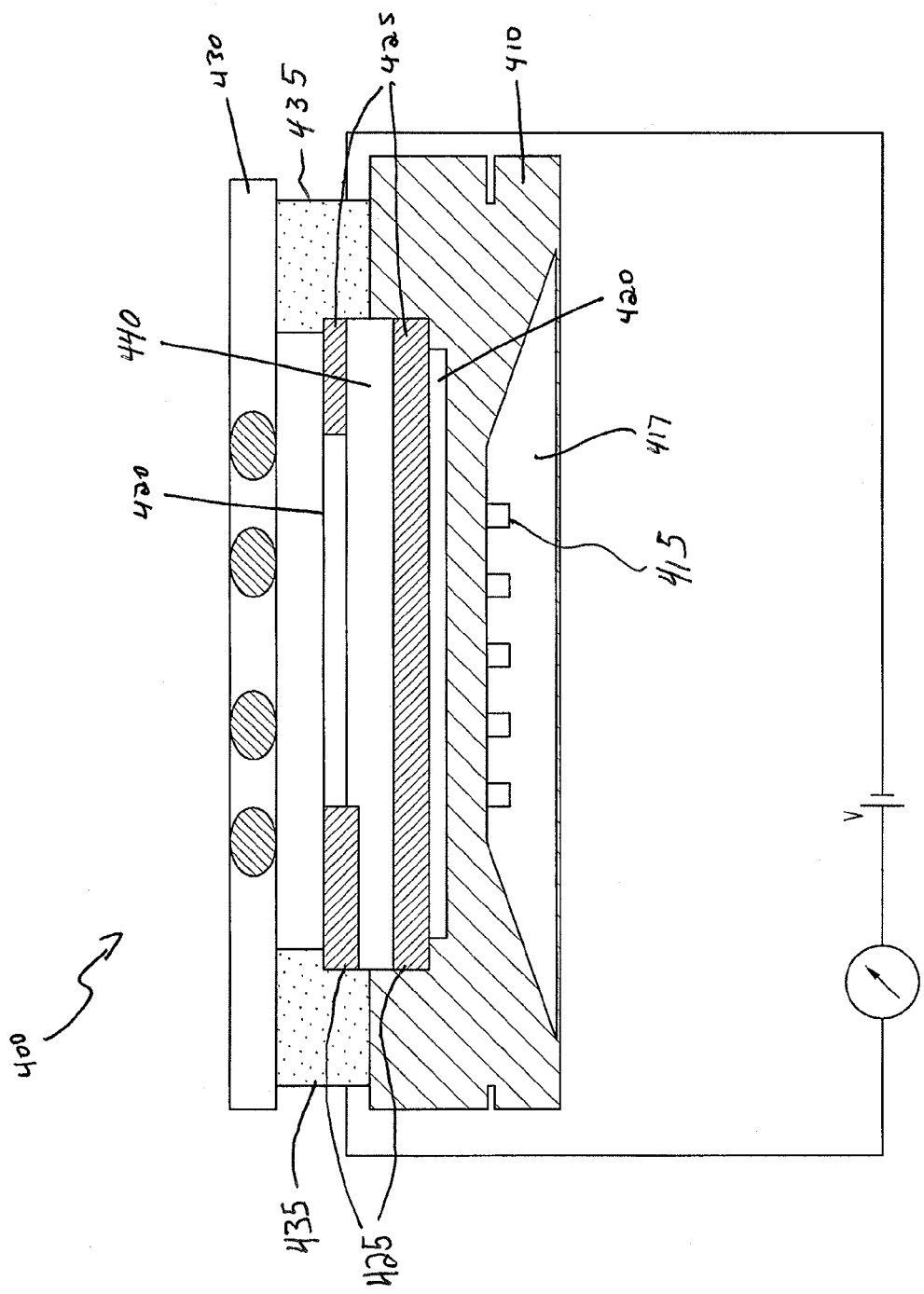
FIG. 10 is a cross-sectional illustration of a microelectromechanical sensor platform according to an exemplary embodiment of the present invention.

As illustrated in FIG. 10, the MEMS sensor platform 400 comprises a substrate 410 and one or more heater and temperature sensors 415 below the surface of the substrate 410 and located in the air gap 417 that is etched out of the substrate 410 in order to thermally isolate the sensing structure and reduce heater power consumption. In one exemplary embodiment, the heater and temperature sensor are embedded on the under side of the substrate 410, whereas in an alternative embodiment, a portion of the substrate on the opposite side of the surface in which a platform will be built is removed, and a heater and sensor is placed on the underside of the substrate 410. One or more sensing layers 420 can be deposited on the substrate sensing element 440. Or alternatively the layer 420 can be a passivating or encapsulating layer. In one exemplary embodiment, the sensing layers are deposited in a pattern comprising bridges and loops to create one or more sensing layers. On the sensing layer, one or more functionalization layers 420 are applied on the sensing element layer. The functionalization layers 420 may comprise one or more nanostructures which can add sensitivity, selectivity and encapsulation to the sensing layer. An overall encapsulation layer 430 may be applied depending on the type of sensor class being built.

In one exemplary embodiment of the present invention, the polysilicon layer is deposited in a pattern on the surface of the substrate in a lock and key electrode pattern. This lock and key pattern comprises an array and allow the electrodes to be used for capacitive and resistive measurements as well as a four-point probe as is illustrated also in FIG. 1. In one exemplary embodiment, the platform can have variable length polysilicon bridges. In this embodiment, the bridges can be used for heating and the sensing layer can be deposited onto an exposed aluminum lead forming a sensing layer as illustrated in FIG. 8B.

Unobtrusive, small, lightweight and energy efficient monitoring devices combining communication equipment and various sensors for detection of hazardous gasses, surrounding environmental conditions and personnel vital signs are possible through utilization of the above detailed MEMS technology. The diminutive size of the device is key to its effectiveness, as a first responder is far more likely to actually utilize a smaller, less obtrusive version of a device when compared to a larger, more interfering device. Another advantage is the energy efficiency of a monitoring device utilizing MEMS technology sensors. For example, a particular MEMS technology carbon monoxide sensor uses less than 10 µW of power. Even in embodiments utilizing a collection of MEMS technology sensors, the power usage for the device, including electronics for communication, amounts to less than 300 µW. Thus, a very small battery may be used to power the monitoring device, further contributing to its overall diminutive size, and thus, its effectiveness.

Particular embodiments of the monitoring device may further incorporate local and remote information readouts and/or alarms controlled by the various sensors and/or the central communication hub. The particular method or variety of alarm is not vital to the present invention, and examples include, but are not limited to, audible, visual and tactile alarms. Particular embodiments of the monitoring device may also incorporate global positioning system (GPS) technology and/or other positioning systems. Positioning system technology provides the central communication hub with first responder position history and tracking information for additional situational understanding. Positioning system technology may also be utilized to inform the central communication hub if any first responder has stopped moving for a particular period of time. While first responders (e.g., firefighters) are obvious users, there will be many other applications for a versatile and ultra low power gas detector with modern communication capability (e.g., wireless and internet based). Many apps will be able to be written around the enabling technology described herein, a major feature is the realization of ultra low power thereby achieving practicality in combining sensors and communication devices heretofore impossible and not realized.

The foregoing description of the various embodiments and principles of the invention has been presented for the purpose of illustration and description. It is not intended to be exhaustive or to limit the invention to the precise forms disclosed. Many alternative, modifications, and variations will be apparent to those skilled in the art. It can be envisioned by one skilled in the art both how to make alternative devices and layers for different functionality and also how to make this structure out of different materials like plastics with different processing tools and capabilities. For example, some principles of the invention may be used in different sensor platform patterns other than bridges. Moreover, although multiple inventive concepts have been presented, such aspects need not utilized in combination, and various combinations of the inventive aspects are possible in light of the various embodiments provided above. We can further provide examples of specific sensors like TCD [thermal conductivity detectors] or ozone or CO or H2S or even antibody detection with the platform described herein. There have been books dedicated to physical, chemical, and biological sensors wherein the functionalization layers are described and these can be interfaced to the MEMS platform described here to provide sensing capability. Accordingly, the above description is intended to embrace all possible alternatives, modifications, combinations and variations that have been discussed or suggested herein, as well as all the others that fall within the principles, spirit and broad scope of the invention as defined by the claims.

I claim:
1. A monitoring device, comprising:
   a. wireless communication equipment; and
   b. at least one sensor or sensing system utilizing microelectromechanical systems (MEMS) technology that consumes less than 500 µW of power;
   wherein data gathered from the at least one sensor or sensing system is transferred by the wireless communication equipment to a node or ultimately to a central communication hub, wherein the at least one sensor or sensing system utilizing MEMS technology comprises at least one surrounding environmental condition sensor configured to detect one or more changes in an environment.

2. The monitoring device of claim 1, wherein the at least one sensor or sensing system utilizing MEMS technology further comprises at least one vital sign sensor.

3. The monitoring device of claim 2, wherein the at least one vital sign sensor senses a vital sign selected from the group consisting of heart rate, body temperature, respiration rate, blood pressure, pulse oximetry and any combination thereof.

4. The monitoring device of claim 1, wherein the at least one sensor or sensing system utilizing MEMS technology comprises at least one gas sensor.

5. The monitoring device of claim 4, wherein the at least one gas sensor senses a gas selected from the group consisting of hydrogen, methane, carbon monoxide, hydrogen sulfide, chlorine, ozone, diesel particulates, gasoline fumes, ethanol, oxygen, carbon dioxide, and combinations thereof.

6. The monitoring device of claim 1, wherein the at least one sensor or sensing system utilizing MEMS technology further comprises at least one surrounding environmental condition sensor.

7. The monitoring device of claim 6, wherein the at least one surrounding environmental condition sensor senses a surrounding environmental condition selected from the group consisting of temperature, pressure, radiation, moisture, and combinations thereof.

8. The monitoring device of claim 1, further comprising at least one of an audible alarm, a visual alarm and/or a tactile alarm.

9. The monitoring device of claim 1, further comprising an integrated global positioning system.

10. The monitoring device of claim 1, wherein the monitoring device is incorporated on or within an earpiece or can be worn on or around the face or human body.

11. The monitoring device of claim 9, wherein the at least one sensor or sensing system utilizing MEMS technology comprises a vital sign sensor and or gas sensor designed for contact with an ear.

12. The monitoring device of claim 10, further comprising at least one hazardous gas sensor or sensing system utilizing MEMS technology.

13. The monitoring device of claim 10, further comprising at least one surrounding environmental condition sensor or sensing system utilizing MEMS technology that results in a sensor with less that 500 uW power.

14. The monitoring device of claim 1, wherein the wireless communication equipment comprises a cellphone.

15. The monitoring device of claim 14, wherein the cellphone further comprises a software application that can receive computed information from the central communications hub to provide communication back to the device worn by the individual.

16. A wearable sensor platforms for awareness, wherein the sensor provides medical alerts through vital signs, other medical sensors, or environmental sensors, wherein the sensor platform comprise less than 500 uWatts power, and wherein the sensor platform comprises at least one MEMS sensor configured to detect one or more chemical changes to an environment.

* * * * *